(12) United States Patent
Bagnis et al.

(10) Patent No.: US 6,287,864 B1
(45) Date of Patent: Sep. 11, 2001

(54) GENE TRANSFER METHOD WITH THE USE OF SERUM-FREE MEDIUM

(75) Inventors: Claude Bagnis; Anne-Marie Imbert; Patrice Mannoni, all of Marseilles (FR)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/463,296

(22) PCT Filed: Jul. 15, 1998

(86) PCT No.: PCT/JP98/03173

§ 371 Date: Jan. 24, 2000

§ 102(e) Date: Jan. 24, 2000

(87) PCT Pub. No.: WO99/05301

PCT Pub. Date: Feb. 4, 1999

(30) Foreign Application Priority Data

Jul. 23, 1997 (JP) .................................................. 9-196772

(51) Int. Cl.[7] .......................... C12N 15/86; C12N 15/63; C12N 7/00; C12N 15/00; A61K 48/00
(52) U.S. Cl. ................. 435/456; 435/235.1; 435/320.1; 435/325; 424/93.2
(58) Field of Search .................................. 435/456, 325, 435/320.1, 235.1; 424/93.2

(56) References Cited

U.S. PATENT DOCUMENTS

| | | | |
|---|---|---|---|
| 4,946,788 | * | 8/1990 | Delespesse ......................... 435/240.7 |
| 5,498,537 | * | 3/1996 | Bresler et al. ...................... 435/235.1 |
| 6,033,907 | * | 3/2000 | Williams ............................... 435/325 |

FOREIGN PATENT DOCUMENTS

| | | |
|---|---|---|
| 0 870 839 A1 | 10/1998 | (EP) . |
| WO 97/18318 | 5/1997 | (WO) . |

OTHER PUBLICATIONS

Sekhar, et al. Human Gene Therapy, vol 7, pp. 33–38, Jan. 1996.*

SEKHAR et al., –XP–000983443 "Retroviral transduction of CD34–enriched hematopoietic progenitors using concentrated vector under serum–free conditions" *BLOOD*, 84(10)358A (1994).

BELLO–FERNANDEX et al., –XP–000983444 "Dendritic cells derived from DC34+ progenitor cells under serum free conditions can be efficiently transduced by a retroviral vector " *BLOOD*, 88(10)429A (1996).

GLIMM et al., –XP–000983315 "Efficient gene transfer into primitive human hematopoietic progenitor cells by a defined, high titer, non–concentrated vector containing medium produced under serum–free conditions", *BLOOD*, 88(10)432A (1996).

IMBERT et al., "Use of serum–free medium for $CD34^+$ cells transductin with retroviral supernatant",*EXPERIMENTAL HEMATOLOGY*, 25(8)894 (1997).

BREEMS et al., "Stroma–conditioned medium and sufficient prestimulation improve fibronectin fragment–mediated retroviral gene transfer into human primitive mobilized peripheral blood stem cells through effects on their recovery and transduction efficiency", *LEUKEMIA*, 12(6)951–959 (1998).

BELLO–FERNANDEZ et al., "Efficient retrovirus–mediated gene transfer of dendritic cells generated from $CD34^+$ cord blood cells under serum–free conditions", *HUMAN GENE THERAPY*, 8:1651–1658 (1997).

* cited by examiner

*Primary Examiner*—David Guzo
*Assistant Examiner*—Gerald G. Leffers, Jr.
(74) *Attorney, Agent, or Firm*—Browdy and Neimark

(57) ABSTRACT

A method for transferring a gene into target cells by a retrovirus with the use of serum-free medium. This method comprises infecting target cells with a retrovirus in serum-free medium optionally containing low-density lipoprotein and/or cytokines in the presence of a functional substance such as fibronectin in an amount effective in elevating the gene transfer efficiency of the retrovirus into the target cells by co-localizing the retrovirus and the target cells.

8 Claims, No Drawings

GENE TRANSFER METHOD WITH THE USE OF SERUM-FREE MEDIUM

CROSS REFERENCE TO RELATED APPLICATION

This present application is the national stage under 35 U.S.C. 371 of PCT/JP98/03173, filed Jul. 15, 1998.

TECHNICAL FIELD

The present invention relates to a gene transfer method with the use of a serum-free medium, more specifically, to a method that elevates the gene transfer efficiency into target cells and enables efficient transformation of the target cells, and to a series techniques concerned therewith in the field of medicine, cell technology, gene technology, developmental technology and the like.

BACKGROUND ART

Mechanisms of a number of human diseases have been elucidated. The recombinant DNA techniques and the techniques for transferring a gene into cells have rapidly progressed. Under these circumstances, protocols for somatic gene therapies for treating severe genetic diseases have been recently developed. More recently, attempts have been made to apply the gene therapy not only to treatment of the genetic diseases but also to treatment of viral infections such as AIDS and cancers.

Most of the gene transfer trials in humans approved by Food and Drug Administration (FDA) to date are ones in which a gene is transferred into cells with the use of a recombinant retrovirus vector. Since the retrovirus vector efficiently transfers the foreign gene of interest into cells and stably integrates the gene into their chromosomal DNAs, it is a preferable means of gene transfer particularly for the gene therapy in which a long-term gene expression is desired. This vector has been subjected to various modifications so as not to have a bad influence on the organism with the transferred gene.

For example, the replication function of the vector is deleted such that the vector used for the gene transfer does not replicate in the cells while repeating unlimited infection (gene transfer). Since such a vector (a replication-deficient retrovirus vector) cannot replicate by itself, a retrovirus in which the vector is encapsidated in a virus particle is generally prepared by using retrovirus producer cells (packaging cells).

Bone marrow cells are the preferable target cells for the somatic gene therapy since they can be handled in vitro and contain hematopoietic stem cells that are capable of self-replicating. It has been demonstrated that umbilical cord blood also contains a number of progenitor cells including hematopoietic stem cells. By performing the gene therapy in which a gene is transferred into such target cells, which are then transplanted into an organism, the transferred gene can be expressed in blood cells for a long period, and a disease can be healed for life.

However, the hematopoietic stem cell is one of the cells into which a gene is not readily transferred with high efficiency, despite of the studies by many groups. To date, the most efficient protocol for gene transfer with respect to hematopoietic stem cells from mice or other animals have been the method in which the hematopoietic stem cells are co-cultured with retrovirus producer cells. However, under the apprehension about safety, gene transfer in cell-free system with a lower risk of contamination of the retrovirus producer cells has been desired for clinical gene therapy methods for humans. Unfortunately, it is not easy to efficiently transfer a gene into hematopoietic stem cells without co-culturing with retrovirus producer cells.

Recently, it was reported that fibronectin, which is a component of the extracellular matrix, or a fragment thereof alone elevates the gene transfer efficiency into cells by a retrovirus (J. Clin. Invest., 93:1451–1457 (1994); Blood, 88:855–862 (1996)). Also, it has been demonstrated that a fibronectin fragment produced by genetic engineering technique has similar properties and can be utilized to efficiently transfer a foreign gene into hematopoietic stem cells (WO 95/26200).

Furthermore, it is disclosed in WO 97/18318 that a functional substance other than fibronectin (such as fibroblast growth factor, collagen etc.) elevates the gene transfer efficiency and that similar increase in the gene transfer efficiency is observed when a mixture of a functional substance having a retrovirus-binding activity and another functional substance having target cell-binding activity is used.

It is believed that the increase in gene transfer efficiency caused by these functional substances is due to the increase in chance of interaction between the retrovirus and the target cells which are co-localized with the aid of the substances.

OBJECTS OF THE INVENTION

In the gene transfer methods using the retrovirus as described above, infection with the retrovirus (i.e., gene transfer) occurs when the target cells are cultured in a medium containing the retrovirus. A medium containing a serum from an animal (in many cases, fetal calf serum (FCS)) is used in this step. Since the serum contains constituents that can serve as nutrients for cells and various growth factors, it is believed that the serum is highly effective for maintaining cells in vitro.

It is believed that the component or the contents of constituents in the serum derived from an animal vary depending on the condition of the health or the like of the animal individual from which the serum was collected. Therefore, reproducible results are not always obtained if the cultivation of the cells and/or the gene transfer is carried out using sera of different lots. Furthermore, since a serum from a heterologous organism other than, for example, a human contains substances antigenic against a human, suitable washing steps are required to decrease the contents of the antigenic substances when the cells maintained in the presence of such a serum are transplanted into a human. In addition, the quality of the serum must be strictly controlled such that the serum does not contain viruses, mycoplasmas or the like.

As described above, the gene transfer methods with the use of serum-containing media have problems, of which the solution is desired.

SUMMARY OF THE INVENTION

The present inventors have studied intensively and surprisingly found that the use of serum-free medium elevates the gene transfer efficiency as compared with a conventional serum-containing medium and that a particularly high gene transfer efficiency is accomplished using a medium to which low-density lipoprotein is added. Thus, the present invention has been completed.

The first invention of the present invention relates to a method for transferring a gene into target cells by a retrovirus, comprising infecting target cells with a retrovirus in serum-free culture medium in the presence of a functional substance in an amount effective in elevating the gene transfer efficiency of the retrovirus into the target cells by co-localizing the retrovirus and the target cells.

There is no limitation regarding the functional substance to be used in the present invention. For example, a substance that has a retrovirus-binding site and a target cell-binding site in a single molecule or a mixture of a molecule that has a retrovirus-binding site and another molecule that has a target cell-binding site can be used. For example, a functional substance such as fibronectin, fibroblast growth factor, collagen and polylysin, or a substance having a retrovirus-binding activity equivalent thereto (e.g., a heparin-binding substance other than those described above) can be used as the functional substance that has the retrovirus-binding site. As the functional substance that has the target cell-binding site, for example, a substance having a ligand that binds to the target cell can be used.

The functional substance preferable to the present invention includes, for example, a fibronectin fragment having a retrovirus-binding site such as a heparin-II-binding region and a cell-binding site such as a binding region to VLA-5 and/or VLA-4. For example, the polypeptide of which the amino acid sequence is shown in the SEQ ID NO:1 of the Sequence Listing (CH-296) is a fibronectin fragment that has a heparin-II-binding region and binding regions to VLA-5 and VLA-4.

There is no limitation regarding a culture medium to be used in the method of the present invention as long as it does not contain a serum. A medium prepared by mixing constituents required for the maintenance and the growth of the cells except the serum can be used. For example, a commercially available serum-free medium may be used. The medium may contain suitable proteins or cytokines. In particular, a medium containing low-density lipoprotein (LDL) is preferable to the present invention.

The second invention of the present invention relates to a cell with a transferred gene, characterized in that the gene is transferred by the method of the first invention. There is no limitation regarding the cell into which the gene is transferred. Various available cells can be used as the target for the gene transfer.

The third invention of the present invention relates to a method of transplanting a cell with a transferred gene into a vertebrate, characterized in that the cell with the transferred gene of the second invention is transplanted into the vertebrate.

The fourth invention of the present invention relates to a culture medium used for transferring a gene, characterized in that the culture medium does not contain a serum and contains a functional substance in an amount effective in elevating the gene transfer efficiency of the retrovirus into the target cells by co-localizing the retrovirus and the target cells.

As the functional substance used for the fourth invention, those as described above can be used. Preferably, for example, the polypeptide of which the amino acid sequence is shown in the SEQ ID NO:1 of the Sequence Listing can be used.

There is no limitation regarding the medium of the fourth invention as long as it does not contain a serum. For example, a commercially available cell culture medium without a serum, preferably, a medium with low-density lipoprotein added can be used. In addition, the medium may optionally contain suitable cytokines.

DETAILED DESCRIPTION OF THE INVENTION

A recombinant retrovirus vector is usually used in the method for transferring a gene of the present invention. In particular, a replication-deficient recombinant retrovirus vector is preferably used. Such a vector is deficient in replication such that it cannot self-replicate in infected cells and is non-pathogenic. A retrovirus into which the vector is packaged can invade into a host cell such as a vertebrate cell (particularly, a mammalian cell) and stably integrates a foreign gene inserted within the vector into the chromosomal DNA.

In the present invention, the foreign gene to be transferred into the cells can be used by inserting it into the retrovirus vector under the control of an appropriate promoter, for example, the LTR promoter or a foreign promoter present in the retrovirus vector. In addition, another regulatory element, such as an enhancer sequence, which cooperates with the promoter and a transcriptional start site, may be present in the vector in order to accomplish the transcription of the foreign gene. Preferably, the transferred gene can additionally accompany a terminator sequence placed downstream the gene.

The foreign gene to be transferred may be a naturally occurring gene or an artificially prepared gene. Alternatively, the foreign gene may be one in which DNA molecules of different origins are joined together by ligation or other means known in the art.

Any gene of which the transfer into cells is desired can be selected as the foreign gene to be inserted into the retrovirus vector. For example, a gene encoding an enzyme or a protein associated with the disease to be treated, an antisense nucleic acid or a ribozyme or a false primer (see, for example, WO 90/13641), an intracellular antibody (see, for example, WO 94/02610), a growth factor or the like can be used as the foreign gene.

The retrovirus vector used in the present invention may have a suitable marker gene that enables the selection of cells with the transferred gene. For example, a drug resistance gene that confers resistance to antibiotics on cells or a reporter gene that makes it possible to distinguish cells with the transferred gene by detecting the enzymatic activity can be utilized as the marker gene.

The vector that can be used includes, for example, known retrovirus vectors such as MFG vector (ATCC No. 68754), α-SGC (ATCC No. 68755) and the like. MFG-nlsLacZ vector (Human Gene Therapy, 5:1325–1333 (1994)), which is used in Examples described below, contains β-galactosidase gene as a marker gene. Thus, cells into which a gene is transferred by means of this vector can be confirmed by examining the enzymatic activity of the gene product using a suitable substrate such as 5-bromo-4-chloro-3-indolyl-β-D-galactoside (X-gal).

These vectors can be prepared as virus particles into which the vectors are packaged by using a known packaging cell line such as PG13 (ATCC CRL-10686), PG13/LNc8 (ATCC CRL-10685), PA317 (ATCC CRL-9078), GP+E-86 (ATCC CRL9642) and GP+envAm-12 (ATCC CRL9641) (U.S. Pat. No. 5,278,056), Psi-Crip (Proc. Natl. Acad. Sci. USA, 85:6460–6464 (1988)) and the like.

A serum-free medium is used in the method of the present invention. As used herein, a serum-free medium means a medium for culturing animal cells which does not contain a serum derived from an animal including a human and is composed of substances of which the constituents are chemically defined. A medium to which a purified and identified substance that constitutes a serum is added is included in the serum-free medium according to the present invention. The basic constituents of such a medium include amino acids, saccharides, energy sources such as organic acids, vitamins, buffering constituents for adjusting pH, inorganic salts and the like. The medium may contain a pH indicator such as phenol red. A known medium such as Dulbecco's Modified Eagle's Medium (DMEM), Iscoves Modified Dulbecco's Medium (IMDM) and the like can be used as the basic medium, which are commercially available, for example, from Gibco-BRL.

Various constituents can be added to these media depending on the type of the target cells for the gene transfer or other objects. For example, various cytokines can be added to the media in order to promote or suppress the growth or the differentiation of the target cells. The cytokine includes interleukines (IL-3, IL-6 etc.), colony-stimulation factors (G-CSF, GM-CSF etc.), stem cell factor (SCF), erythropoietin, various cell growth factors and the like. Many of these cytokines derived from humans are commercially available. Upon using these cytokines, one having the activity of interest is selected, and optionally used in combination with another.

Furthermore, the present inventors have demonstrated that particularly excellent gene transfer efficiency is accomplished when low-density lipoprotein (LDL) is added to the medium. Low-density lipoprotein derived from human is commercially available, for example, from Sigma. As shown in Examples described below, when a gene transfer into cells by means of a supernatant containing a retrovirus is performed in a serum-free medium containing low-density lipoprotein, a higher gene transfer efficiency is accomplished as compared with that accomplished with a conventional serum-containing medium. In addition, gene transfer can be performed with still higher efficiency in the presence of the functional substance as described below.

The present invention is characterized in that target cells are infected with a retrovirus in the presence of a functional substance which can elevate the gene transfer efficiency of the retrovirus into the target cells by co-localizing the retrovirus and the target cells.

Cells with the transferred gene can be obtained with high efficiency when the cells are infected with the retrovirus in the presence of an effective amount of the functional substance. For example, the functional substances as described in WO 95/26200 and WO 97/18318 can be used as the functional substance.

As used herein, an effective amount is an amount effective to result in transformation of target cells through the gene transfer into the target cells by a retrovirus. A suitable amount is selected depending on the functional substance to be used and the type of the target cells. The amount can be determined, for example, by measuring the gene transfer efficiency by the method as described herein. In addition, gene transfer efficiency means the efficiency of transformation.

There is no limitation regarding the functional substance having the retrovirus-binding site to be used in the present invention. For example, heparin-II-binding region of fibronectin, fibroblast growth factor, collagen, polylysin and the like, as well as a substance functionally equivalent to these functional substances such as a functional substance having a heparin-binding site can be used. Furthermore, a mixture of the functional substances, a polypeptide containing the functional substance, a polymer of the functional substance, a derivative of the functional substance or the like can be used.

There is no limitation regarding the functional substance having the target cell-binding site to be used in the present invention. The functional substance includes a substance that has a ligand that binds to the target cell. The ligand includes a cell adhesive protein, a hormone or a cytokine, an antibody against a cell surface antigen, a polysaccharide or a glycoprotein, a sugar chain in a glycolipid, a metabolite of the target cell and the like. Furthermore, a polypeptide containing the functional substance, a polymer of the functional substance, a derivative of the functional substance, a functional equivalent of the functional substance or the like can be used.

The functional substance as described above can be obtained from naturally occurring substances, prepared artificially (for example, by recombinant DNA techniques or chemical synthesis techniques), or prepared by combining a naturally occurring substance and an artificially prepared substance. In addition, a mixture of a functional substance that has a retrovirus-binding site and another functional substance that has a target cell-binding site can be used for the gene transfer using the functional substances as described in WO 97/18318. Alternatively, a functional substance that has a retrovirus-binding site and a target cell-binding site in a single molecule, which may be selected or prepared, can be used.

In the method of the present invention, for example, fibronectin, a fibronectin fragment or a mixture thereof can be used. These functional substances can be either naturally occurring or prepared by chemical synthesis. They can be prepared in a substantially pure form from naturally occurring substances by a method as described, for example, in J. Biol. Chem., 256:7277 (1981), J. Cell Biol., 102:449 (1986) or J. Cell Biol., 105:489 (1987). In this regard, fibronectin or a fibronectin fragment as used herein means one that is substantially free of another protein naturally associated with fibronectin.

Furthermore, useful information regarding the fibronectin fragment which can be used herein or the preparation thereof is described in J. Biochem., 110:284–291 (1991), which further reports the above-mentioned recombinant fragment); EMBO J., 4:1755–1759 (1985), which reports the structure of the human fibronectin gene; and Biochemistry, 25:4936–4941 (1986), which reports the heparin-II-binding region of human fibronectin.

The fibronectin or the fibronectin fragment as described herein can be prepared from recombinant cells as described generally, for example, in U.S. Pat. No. 5,198,423. Specifically, a fibronectin fragment containing the heparin-II region, which is a retrovirus-binding site, such as CH-296 (the amino acid sequence is shown in the SEQ ID NO:1 of the Sequence Listing) which is used in Examples described below and recombinant polypeptides such as H-271, H-296, CH-271 and the like as well as the method for obtaining them are described in detail in the specification of the above-mentioned patent. These fragments can be obtained by culturing *Escherichia coli* strains deposited under accession number FERM P-10721 (H-296) (the date of the original deposit: May 12, 1989), FERM BP-2799 (CH-271) (the date of the original deposit: May 12, 1989), FERM BP-2800 (CH-296) (the date of the original deposit: May 12, 1989) and FERM BP-2264 (H-271) (the date of the original deposit: Jan. 30, 1989) at the National Institute of Bioscience and Human-Technology, Agency of Industrial Science and Technology, Ministry of International Trade and Industry, 1–3, Higashi 1-chome, Tsukuba-shi, Ibaraki-ken, Japan, as described in the publication. In addition, fragments that can be typically derived from these fragments can be prepared by modifying the plasmids harbored in these *Escherichia coli* strains by known recombinant DNA techniques. Among the fibronectin fragments described above, H-296 has a polypeptide of binding region to VLA-4, CH-271 has a peptide of binding region to VLA-5, and CH-296 has both of them (Nature Medicine, 2:876–882 (1996)).

As described in Examples below, the gene transfer efficiency in a serum-free medium is elevated in the presence of the fibronectin or the fibronectin fragment CH-296. Also, a similar gene transfer efficiency can be accomplished by using, for example, a mixture of H-271, which is a fibronectin fragment having a retrovirus-binding region, and C-271, which is a fibronectin fragment having a cell-binding activity, as described in WO 97/18318.

By infecting cells with a retrovirus in a serum-free medium in the presence of an effective amount of the fibronectin, the fibronectin fragment or the mixture thereof, cells with transferred genes can be efficiently obtained. The fibronectin, the fibronectin fragment or the mixture thereof may be immobilized on the surface of the culture vessel used for the infection with the retrovirus, for example. The infection with the retrovirus can be performed according to a conventional method, for example, by incubation at 37° C. in 5% $CO_2$. The conditions and the incubation time may suitably changed depending on the target cells or the objects.

Target cells are not infected with a retrovirus when they are in $G_0$ phase. Therefore, it is preferable to induce the cells into the cell cycle by pre-stimulating them. For this purpose, the target cells are cultured in the presence of a suitable target cell growth factor before infecting the cells with the retrovirus. For example, a target cell growth factor such as interleukin(IL)-6, stem cell factor and the like is used to pre-stimulate bone marrow cells or hematopoietic stem cells for gene transfer.

There is no limitation regarding the cell to be used as the target for the gene transfer by the method of the present invention. For example, stem cells, hematopoietic cells, non-adhesive low-density mononuclear cells, adhesive cells, bone marrow cells, hematopoietic stem cells, peripheral blood stem cells, umbilical cord blood cells, fetal hematopoietic stem cells, embryogenic stem cells, embryonic cells, primordial germ cells, oocytes, oogonia, ova, spermatocytes, sperms, CD34+ cells, c-kit+ cells, pluripotent hematopoietic precursor cells, unipotent hematopoietic precursor cells, erythroid precursor cells, lymphoid mother cells, mature blood cells, lymphocytes, B cells, T cells, fibroblasts, neuroblasts, neurocytes, endothelial cells, vascular endothelial cells, hepatocytes, myoblasts, skeletal muscle cells, smooth muscle cells, cancer cells, myeloma cells, leukemia cells and the like can be used. The method of the present invention is preferably utilized for hematopoietic cells that are available from blood and bone marrow because these cells are relatively easy to obtain and because the techniques for culturing and maintaining them are established.

Particularly, if a long-term expression of the transferred gene is intended, blood precursor cells such as hematopoietic stem cells, CD34+ cells, c-kit+ cells, pluripotent hematopoietic precursor cells and the like are suitable as target cells.

By using the fibronectin or the fibronectin fragment (especially, the fibronectin fragment having the binding site to VLA-5 and/or VLA-4 as a cell-binding site) as the functional substance, the gene can be efficiently transferred into cells expressing VLA-5 and VLA-4 on their cell surface such as hematopoietic stem cells and CD34+ cells.

As described above, the cells into which a gene is transferred by the method of the present invention can be transplanted into an organism, thereby enabling a gene therapy in which a foreign gene is expressed in vivo. Since the cells with the transferred gene obtained by the method of the present invention do not contain proteins or impurities derived from a serum from a heterologous animal, they are suitable for transplantation into an organism. For example, a gene therapy using hematopoietic stem cells as target cells can be carried out by the following procedure.

First, a material containing hematopoietic stem cells, such as bone marrow tissue, peripheral blood, umbilical cord blood and the like, is collected from a donor. Although such a material can be directly used in the gene transfer procedure, mononuclear cell fractions containing hematopoietic stem cells are usually prepared by means of density gradient centrifugation and the like, or hematopoietic stem cells are further purified by utilizing cell surface marker molecules such as CD34 and/or c-kit. The material containing the hematopoietic stem cells is infected with a recombinant retrovirus vector, into which a gene of interest is inserted by the method of the preset invention, after being pre-stimulated by using a suitable cell growth factor, if necessary. The cells with the transferred gene thus obtained can be transplanted into a recipient, for example, by intravenous administration. Although the recipient is preferably the donor itself, allogenic transplantation can be performed. For example, if the umbilical cord blood is used as the material, the allogenic transplantation is carried out.

Some of the gene therapies using hematopoietic stem cells as the target cells are for complementing a deficient or abnormal gene in a patient, for example, the gene therapy for ADA deficiency or Gaucher's disease. In addition, a drug resistance gene may be transferred into the hematopoietic stem cells in order to alleviate the damage of hematopoietic cells due to the chemotherapeutic agents used for the treatment of cancer or leukemia, for example.

A tumor vaccination therapy, in which a gene for a cytokine is transferred into cancer cells, the ability of the cancer cells to proliferate are deprived, and the cells are then returned to the body of the patient to enhance the tumor immunity, is investigated as a gene therapy for cancer (Human Gene Therapy, 5:153–164 (1994)). In addition, attempts are made to treat AIDS by a gene therapy. In this case, a procedure in which a gene encoding a nucleic acid molecule (e.g., an antisense nucleic acid or a ribozyme) which interferes with the replication or the gene expression of HIV (human immunodeficiency virus) is transferred into T cells infected with HIV, which is the causal agent of AIDS, is considered (e.g., J. Virol., 69:4045–4052 (1995)).

As described in Examples below, cells with a transferred gene can be obtained with high efficiency by using the gene transfer method of the present invention. Since the preparation of the cells thus obtained do not contain a serum derived from a heterologous organism, the cells can be transplanted into an organism without additionally performing a special procedure. Furthermore, since the component and the contents of the constituents in the medium do not vary as compared with those in media used in conventional methods, reproducible gene transfer can be accomplished.

The following Examples illustrate the present invention in more detail, but are not to be construed to limit the scope thereof.

EXAMPLE 1

Preparation of CH-296

A polypeptide derived from human fibronectin, CH-296 (the amino acid sequence is shown in the SEQ ID NO:1 of the Sequence Listing), was prepared from *Escherichia coli* HB101/pCH102 (FERM BP-2800) containing the recombinant plasmid pCH102, which contains the DNA encoding the polypeptide, according to the method as described in U.S. Pat. No. 5,198,423.

EXAMPLE 2

Immobilization of Fibronectin and CH-296 onto a Plate

Fibronectin (Sigma) and CH-296 prepared as described in Example 1 were dissolved in phosphate buffered saline (PBS, BioWhittaker) to 50 µg/ml and 100 µg/ml, respectively, then filtered through 0.22-µm filters (Minisarto filter 0.22 µm, Sartorius). 1 ml of CH-296 solution or fibronectin solution was added to a well of 12-well plate (Falcon). The plate was then incubated at room temperature for 2 hours for immobilization. The solution subjected to the immobilization was exchanged for 2 ml per well of PBS containing 2% bovine serum albumin (BSA, Sigma). The plate was then incubated for further 30 minutes at room temperature. After incubation, the plate was washed twice with Hanks' buffered salt solution (Gibco-BRL) containing 25 mM HEPES (Gibco-BRL).

EXAMPLE 3

Preparation of Virus Supernatant

DMEM medium (BioWhittaker) containing 10% calf serum (JRH Bioscience) and 100 units/ml penicillin—100 μg/ml streptomycin (Gibco-BRL) was used for culturing A7.21 cells derived from Psi-Crip cells (Proc. Natl. Acad. Sci. USA, 85:6460–6464 (1988)), which produce the retrovirus vector MFG-nlsLacZ (Human Gene Therapy, 5:1325–1333 (1994)). $3 \times 10^6$ A7.21 cells were inoculated into 100-mm dishes for tissue culture (Falcon) and cultured overnight. The medium was then removed and replaced by 5 ml of RPMI medium (BioWhittaker) containing 10% fetal calf serum (FCS, BioWhittaker) or 5 ml of BIT-9500 medium (Stem Cell Technologies) containing 40 μg/ml of low-density lipoprotein (LDL, Sigma). After cultivation for 24 hours, the culture supernatants were collected and filtered through 0.45-μm filters (Minisarto filter 0.45 μm, Sartorius). Interleukin-3 (IL-3, Amgen), interleukin-6 (IL-6, Amgen) and Stem Cell Factor (SCF, Amgen) were added to the culture supernatants to 10 ng/ml, 10 ng/ml and 100 ng/ml, respectively.

The titers of the virus solutions thus obtained were $1.7 \times 10^7$ pfu/ml for RPMI medium containing 10% FCS and $1.8 \times 10^6$ pfu/ml for BIT-9500 medium containing 40 μg/ml of LDL as measured using Rat2 cells (ATCC CRL-1764) according to the method as previously reported (Cancer Gene Therapy, 4:5–8 (1997)).

EXAMPLE 4

Isolation of CD34+ Cells

CD34+ cells were isolated from human peripheral blood mobilized by chemotherapeutics and G-CSF (Human Gene Therapy, 5:1325–1333 (1994)) by using immunological magnetic separation method (Magnetic-Activated Cell Sorting, Miltenyi Biotec). The purity of the resulting CD34+ cells was 95%.

EXAMPLE 5

Gene Transfer into CD34+ Cells (1) Gene transfer by supernatant method

CD34+ cells were pre-stimulated prior to infection with a retrovirus.

Specifically, The CD34+ cells prepared in Example 4 were incubated in the presence of 10 ng/ml of IL-3, 10 ng/ml of IL-6 and 100 ng/ml of SCF in either RPMI medium containing 10% FCS or BIT-9500 medium containing 40 μg/ml of LDL for 48 hours. $3 \times 10^5$ pre-stimulated CD34+ cells were suspended in the virus solutions prepared in Example 3. The virus solutions were selected such that the medium used for preparing the virus solution was the same as that used for pre-stimulating the CD34+ cells. The cell suspensions were added to wells with nothing immobilized (untreated wells), wells with the immobilized fibronectin prepared in Example 2, and wells with the immobilized CH-296 in a 12-well plate. The cells were cultured in the presence of 5% $CO_2$ at 37° C. for 2 hours. Polybrene (4 μg/ml, Sigma) were added to the untreated wells and the wells with the immobilized fibronectin. After 2 hours, new virus solutions (containing IL-3, IL-6 and SCF at the above-mentioned concentrations) were added and the cells were cultured in the presence of 5% $CO_2$ at 37° C. for further 22 hours. After cultivation, the cells were collected by using a cell detachment buffer, suspended in RPMI medium containing 10% FCS or BIT-9500 medium containing 40 μg/ml of LDL, then cultured for 24 hours.

(2) Gene transfer by co-cultivation

On the day before the start of the co-cultivation, A7.21 cells were treated with 10 μg/ml of ametycine (Choay-Sanofi) for 2 hours, then collected using trypsin/EDTA (Gibco-BRL). The cell suspension corresponding to $2 \times 10^5$ cells was added to a 12-well plate. CD34+ cells were pre-stimulated in the presence of 10 ng/ml of IL-3, 10 ng/ml of IL-6 and 100 ng/ml of SCF in either RPMI medium containing 10% FCS or BIT-9500 medium containing 40 μg/ml of LDL for 24 hours. $10^5$ pre-stimulated CD34+ cells were added to the wells to which the A7.21 cells had been added, and cultured in the presence of 10 ng/ml of IL-3, 10 ng/ml of IL-6, 100 ng/ml of SCF and 4 μg/ml of polybrene in the medium used for the pre-stimulation (1 ml/well). After 72 hours, non-adhesive cells were collected and suspended in IMDM medium (BioWhittaker).

EXAMPLE 6

Assessment of Gene Transfer 250 cells with the transferred gene obtained in Example 5 were added per plate containing 0.5 ml of semisolid medium (Methocult H4230, Stem Cell Technologies) containing 0.9% methyl cellulose, 30% FCS, 1% BSA, 0.1 mM mercaptoethanol and 2 mM glutamine (procedures were performed in triplicate). 2 units/ml of erythropoietin (Amgen), 10 ng/ml of GM-CSF (Amgen), 10 ng/ml of G-CSF (Amgen), 10 ng/ml of SCF, 10 ng/ml of IL-3 and 10 ng/ml of IL-6 were added to the medium.

The gene transfer efficiency was calculated from the enzymatic activity of β-galactosidase expressed from the nlsLacZ gene. After cultivation for 21 days, the plates were directly stained with X-Gal (5-bromo-4-chloro-3-indolyl-β-D-galactoside). The number of colonies stained with blue color was counted to determine the ratio of the stained colonies against the total colonies.

The ratio of X-Gal positive colonies thus determined is shown in Table 1.

TABLE 1

|  | RPMI + FCS | BIT + LDL |
| --- | --- | --- |
| Untreated well | 4.8% | 15.5% |
| Fibronectin-immobilized well | 14.1% | 24.6% |
| CH-296-immobilized well | 11.8% | 33.6% |
| Co-cultivation method | 29.6% | 22.3% |

The results described above demonstrate that the combination of the fibronectin or the fibronectin fragment CH-296 and BIT-9500 medium containing LDL (i.e., a serum-free medium) enables the gene transfer with high efficiency.

What is claimed is:

1. A method for transferring a gene into target hematopoietic stem cells by a retrovirus, comprising infecting target hematopoietic stem cells with a retrovirus in serum-free culture medium in the presence of low density lipoprotein and a functional substance which has a retrovirus-binding site and a target cell-binding site in an amount effective in elevating the gene transfer efficiency of the retrovirus into target hematopoietic stem cells by co-localizing the retrovirus and hematopoietic stem cells, wherein the functional substance is fibronectin, a fragment of fibronectin, or a mixture of fibronectin fragments.

2. The method according to claim 1, wherein the functional substance is a fragment of fibronectin having the amino acid sequence as shown in the SEQ ID NO:1 of the Sequence Listing.

3. The method according to claim 1, wherein the functional substance is immobilized onto a culture vessel.

4. The method according to claim 1, wherein the culture medium contains a cytokine.

5. The method according to claim 4, wherein the culture medium contains a cytokine selected from the group consisting of IL-3, IL-6 and SCF.

6. The method according to claim 1, wherein the hematopoietic stem cells are CD34+ cells.

7. The method according to claim 1, wherein the retrovirus is a recombinant retrovirus containing a foreign gene.

8. The method according to claim 7, wherein the retrovirus is a replication-deficient recombinant retrovirus.

* * * * *

SEQUENCE LISTING

<160> NUMBER OF SEQ ID NOS: 1

<210> SEQ ID NO 1
<211> LENGTH: 574
<212> TYPE: PRT
<213> ORGANISM: Homo sapiens

<400> SEQUENCE: 1

```
Pro Thr Asp Leu Arg Phe Thr Asn Ile Gly Pro Asp Thr Met Arg Val
 1               5                  10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
                260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
                340                 345                 350

Leu Lys Asp Thr Leu Thr Ser Arg Pro Ala Gln Gly Val Val Thr Thr
```

-continued

```
                355                 360                 365
Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
        515                 520                 525

Ile Tyr Val Ile Ala Leu Lys Asn Asn Gln Lys Ser Glu Pro Leu Ile
    530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
                565                 570
```